US009207205B2

(12) United States Patent
Ma et al.

(10) Patent No.: US 9,207,205 B2
(45) Date of Patent: Dec. 8, 2015

(54) METHOD AND APPARATUS FOR CANCER SCREENING

(75) Inventors: Yinfa Ma, Rolla, MO (US); Stephen Gibbons, St. James, MO (US)

(73) Assignee: The Curators of the University of Missouri, Columbia, MO (US)

( * ) Notice: Subject to any disclaimer, the term of this patent is extended or adjusted under 35 U.S.C. 154(b) by 157 days.

(21) Appl. No.: 12/971,194

(22) Filed: Dec. 17, 2010

(65) Prior Publication Data
US 2011/0147217 A1 Jun. 23, 2011

Related U.S. Application Data

(60) Provisional application No. 61/284,336, filed on Dec. 17, 2009.

(51) Int. Cl.
| G01N 27/447 | (2006.01) |
| G01N 21/64 | (2006.01) |
| G01N 33/52 | (2006.01) |
| G01N 33/53 | (2006.01) |

(52) U.S. Cl.
CPC ........ *G01N 27/44721* (2013.01); *G01N 21/645* (2013.01); *G01N 33/52* (2013.01); *G01N 33/5308* (2013.01)

(58) Field of Classification Search
CPC . G01N 21/645; G01N 33/5308; G01N 33/52; G01N 33/50; G01N 27/44721; G01N 27/447
USPC ........... 204/51, 452, 461, 450, 600, 601, 603, 204/612; 356/344, 128–146
See application file for complete search history.

(56) References Cited

U.S. PATENT DOCUMENTS

| 6,576,105 B1 * | 6/2003 | Ma ................................ 204/451 |
| 7,090,758 B2 * | 8/2006 | Mathies et al. ............... 204/452 |
| 7,402,422 B2 * | 7/2008 | Fuchs et al. ................. 435/283.1 |
| 2002/0167665 A1 | 11/2002 | Yeung et al. |

FOREIGN PATENT DOCUMENTS

EP 0608570 A1 8/1994

OTHER PUBLICATIONS

Tomandl et al., J.Sep.Sci. 2003, 26, 674-678.*
Meras et al., Anal Biochem, 346, 2005, 201-209.*
Trehan et al., A rapid assay for urinary pteridine levels for monitoring cancer, J. Clin. Biochem. Nutr. 14, 195-2013, 1993.*
Fukushima et al., Analytical Biochemistry 102, 176-188, 1980.*
Merás et al., Analytical Biochemistry, 2005, 346, 201-209.*
Fuller et al., "Single Neuron Analaysis by Capillary Electrophoris with Fluorescence Spectroscopy", Neuron, Feb. 1998, vol. 20, Issue 2, pp. 173-181.
Stea et al., "Urinary excretion levels of unconjugated pterins in cancer patients and normal individuals", Clinica Chimica Acta, Jul. 1, 1981, vol. 113, Issue 3, pp. 231-242.
Gibbons et al., "Optimization of urinary pteridine analysis conditions by CE-LIF for clinical use in early cancer detection", Electrophoresis, 2009, vol. 30, Issue 20, pp. 3591-3597 (Oct. 27, 2009).
Gamagedar et al., "Investigation of urinary pteridine levels as potential biomarkers for noninvasive diagnosis of cancer", Clinica Chimica Acta, vol. 412, Issue 1-2, pp. 120-128.

(Continued)

*Primary Examiner* — Gurpreet Kaur
(74) *Attorney, Agent, or Firm* — Senniger Powers LLP

(57) ABSTRACT

A method and apparatus for detection of pteridine levels in a biological sample using CE-LIF which is useful for early cancer screening involving fully oxidizing pteridine compounds in a sample such as a urine sample, subjecting to CE-LIF to assess compound concentration, and compare to expected levels in for healthy or cancer-bearing patients.

11 Claims, 9 Drawing Sheets

(56) References Cited

OTHER PUBLICATIONS

Han, "Pteridine Analysis in Urine by Capillary Electrophoresis Using Laser-Induced Fluorescence Detection", Analytical Chemistry, 1999, vol. 71, No. 7, Apr. 1, pp. 1265-1269.

Hibiya, et al., "Interference of a Methotrexate Derivative with Urinary Oncopterin [N2-( 3-aminopropyl)biopterin] Measurement by High-Performance Liquid Chromatography with Fluorimetric Detection," Journal of Chromatography B, 691, 1997 ~, pp. 223-227.

* cited by examiner

METHOD AND APPARATUS FOR CANCER SCREENING

CROSS REFERENCE TO RELATED APPLICATIONS

This application claims priority from U.S. Provisional Application Ser. No. 61/284,336, which has a filing date of Dec. 17, 2009.

FIELD OF THE INVENTION

The present invention generally relates to an apparatus and method for screening for cancer. In particular, the apparatus and method for screening for cancer is based on the detection of pteridine molecules in biological samples, for example, urine samples.

BACKGROUND OF THE INVENTION

Cancer is the second leading cause of death in the United States. To date, approximately 50% of all neoplasms are treated with multi-disciplinary cancer treatment. Neoplastic disorders differ widely in etiology, pathology, and natural disease history. The principle behind detection at earlier stages of disease progression yielding higher cure rates applies to virtually all solid tumors. As a result, cancer screening has been an area of elevated research and clinical interest and has greatly impacted cancer diagnoses and treatments.

Biomarkers are compounds in the body that may be indicative of medical conditions or biological states. Hayes et al. defined a cancer biomarker as "a molecular, cellular, tissue, or process-based alteration that provides indication of current, or more importantly, future behavior of cancer." See Hayes D F, Bast R C, Desch C E, et al. Tumor marker utility grading system: a framework to evaluate clinical utility of tumor markers. J. Natl. Cancer Inst. 1996, 88, pp. 1456-66. These biological and physiological indicators could include a broad range of biochemical entities, such as nucleic acids, proteins, sugars, lipids, and small metabolites, as well as whole cells, in either specific tissues or in circulation. Today, circulating cancer cells are becoming a powerful tool in "microscopic" cancer screening. Detection of biomarkers, either individually or as larger sets or patterns, can be accomplished by a wide variety of methods, ranging from biochemical analysis of blood or tissue samples to biomedical imaging.

Normally, patients are hesitant to damage their organs and tissues to give samples during the disease diagnosis process. They may also be reluctant to give blood for diagnostic tests. Therefore, development of a noninvasive diagnostic technique for early cancer screening is very crucial for all populations. Noninvasive diagnosis involves procedures that do not penetrate the body mechanically, nor break the skin or involve penetration through a body cavity. It does not require an incision into the body or the removal of biological tissue. Currently, many researchers are focusing on noninvasive means to diagnose cancer by analyzing cancer biomarkers in urine, which is more easily collected than tissue or blood samples.

Recently, pteridine molecules have become a focal point of cancer screening research. See Rokos K., Rokos H., Frisius H., Huefner M., Pteridines in Cancer and Other Diseases, 1983, pp. 153-7; Noronha J. M., Trehan S., Urinary Excretion of Total Pteridines in Cancer, 1990, pp. 515-8; Murr C., Widner B., Wirleitner B., Fuchs D., Neopterin as a Marker for Immune System Activation, Curr. Drug. Metab. 2002, 3, pp. 175-87; Han F., Huynh B. H., Shi H., Lin B., Ma Y., Pteridine Analysis in Urine by Capillary Electrophoresis Using Laser-Induced Fluorescence Detection, Anal. Chem., 1999, 71, pp. 1265-9; Gibbons S. E., Stayton I., Ma Y., Optimization of Urinary Pteridine Analysis Conditions by CE-LIF for Clinical Use in Early Cancer Detection, Electrophoresis, 2009, 30, pp. 3591-7; Fuchs D., Kramer A., Reibnegger G., et al., Neopterin and Beta 2-Microglobulin as Prognostic Indices in Human Immunodeficiency Virus Type 1 Infection, Infection, 1991, 19 (Suppl. 2), pp. S98-S102. Pteridines are a group of heterocyclic compounds contained in the body and excreted in the urine. Research into the use of pteridines as cancer biomarkers investigated the urinary pteridine levels as potential biomarkers for noninvasive diagnosis of cancer. Pteridines are naturally occurring heterocyclic compounds involved in the biosynthetic pathways of cofactors and vitamins. Research suggests that concentrations of pteridines found in urine differ between cancer patients and non-cancer patients. For example, it has been reported that the neopterin/biopterin ratio differs among cancer patients and non-cancer patients. See Stea, B. et al., Clin. Chim. Acta, 1981, 113, pp. 231-242, which reported that the neopterin/biopterin level for cancer patients was 1.6 times that of normal subjects. Additionally, the amount of pteridine and pattern of expression in the urine may vary with specific neoplasms and clinical stage. Thus, urinary pteridine assays have been studied as a potential cancer screening method Analysis of pteridines has been performed with several techniques, such as thin layer chromatography (TLC), high performance liquid chromatography (HPLC) combined with UV or fluorescence detection, and conventional capillary electrophoresis with laser induced fluorescence detection (CE-LIF). For example, a method has been reported describing the determination of total oncopterin, neopterin, and biopterin in human urine using solid phase extraction with 6,7-dimethylpterin as internal standard and gradient HPLC with fluorescence detection. See Tomandl et al., Journal of Separation Science, Vol. 26, 8, pp. 674-678, June 2003. However, the detection limit for oncopterin reported in the study is relatively high at about 1.43 mol/L. Moreover, the reported urine preparation time is still long (about 2 hr), since the study utilized full hydrolysis vs. oxidation of the pteridines.

In U.S. Pat. No. 6,576,105 B1 by Yinfa Ma, the inventor also described a detection method for pteridines in urine using the conventional CE-LIF technology. Even though the patented CE-LIF technology has shown promising improvements in feasibility for clinical laboratories, the patented CE-LIF technology has limitation on the accuracy and reproducibility because of the complexity of urine samples.

Therefore, there is a need to provide a new and improved cancer screening method by pteridine urine detection using CE-LIF. There is also a need to provide an improved CE-LIF apparatus for the pteridine urine detection to achieve a noninvasive, sensitive, fast, simple, and cost effective cancer screening tool.

SUMMARY OF THE INVENTION

The present invention is directed to a cancer screening method. The cancer screening method of the present invention detects pteridine concentration levels in a subject's biological sample such as urine. The concentration of the pteridine compound in the patient's biological sample is compared to an expected concentration of the pteridine compound in either a healthy mammal of the same species or in a cancer-bearing mammal of the same species.

According to some embodiments of the invention, the inventive cancer screening method comprises the step of detecting oncopterin level in a subject's urine sample.

The inventive method may further comprise the step of detecting concentration levels of other pteridine to determine what type(s) of cancer that a subject may develop.

According to some embodiments of the method of the present invention, a biological sample, e.g., a subject's urine sample, is collected and pretreated prior to analysis. Pretreatment involves a first step of oxidizing the pteridines in the sample by exposure to a composition containing an oxidizing agent. Pteridines are oxidized to their fully oxidized state. In some preferred embodiments, the oxidizing agent is iodine. Pretreatment may involve alkalinization of the pteridine containing sample by exposure to an alkaline solution, which assists in the extraction of the pteridines from the urine sample as pteridines have a higher solubility factor in alkaline solutions.

According to the method of the present invention, the sample may be centrifuged and the supernatant diluted with a buffer solution in order to prepare the sample for separation via capillary electrophoresis. The treated sample is then introduced subjected to capillary electrophoresis by using either a gravimetric, electrokinetic, or pressure injection technique. The separated sample is then irradiated by a non-polarizing light source, and the fluorescence emission is detected by a fluorescence detection means, such as a photomultiplier tube, to collect the fluorescence.

The present invention is further directed to a capillary electrophoresis lased induced fluorescence (CE-LIF) apparatus. The CE-LIF employs a combination of lenses, filters, and irises to enhance stability and reproducibility of the urine pteridine detection. The lenses, filters, and irises enhance detection by substantially reducing laser scatter from the excitation source and from the capillary, thereby producing a stable, low noise baseline that enables low limits of detection. The CE-LIF apparatus employs a combination of a confocal lens having greater than 10× magnification placed in the range of 45 to 90 degrees from the laser path to collect and focus fluorescence emission from the sample. The CE-LIF apparatus employs at least one physical iris for removing scattered light either from the filtered non-polarized laser or from any fluorescence generated by the device. A device structured with the high magnification confocal lens and iris yields a very low noise baseline, enabling low limits of detection of pteridines in urine and other samples.

In some embodiments, the inventive apparatus includes 1) a non-polarized excitation source emitting non-polarized laser at a non-traditional solid state laser wavelength. In some embodiments, the inventive apparatus includes 2) a first filtration means for filtering the non-polarized laser. In some embodiments, the inventive apparatus includes 3) a focal lens that focuses the filtered, non-polarized laser onto a capillary, the pathway by which the intended sample is separated and exposed to the filtered, non-polarized laser via a detection window on the capillary. In some embodiments, the inventive apparatus includes 4) a sample holder with a detection window that facilitates the mounting of an electrophoresis capillary. In some embodiments, the inventive apparatus includes 5) a capillary electrophoresis device that is capable of separating the specific compounds of interest (pteridines) within the samples and delivering the sample to the detection window of the capillary mounted within the sample holder.

In some embodiments, the inventive apparatus includes 6) a confocal lens greater than 10× magnification placed in the range of 45 to 90 degrees from the laser path to collect and focus fluorescence emission from the sample. In some embodiments, the inventive apparatus includes 7) a second filtration means for filtering non-pteridine fluorescence generated by any compound other than those in the pteridine family or for filtering background scattering light from the laser. In some embodiments, the inventive apparatus includes 8) a physical iris for removing any scattering either from the filtered non-polarized laser or from any fluorescence generated by the device. The physical iris controls the light beam size and minimizes the scattered light. In some embodiments, the inventive apparatus includes 9) a detection means for detecting the filtered fluorescence emission generated by the pteridines in the samples. In some embodiments, the inventive apparatus includes 10) a current to voltage (I to V) converter to communicate the raw output from the electrons from the compounds of interest undergoing fluorescent decay to the digital input of the device collecting the output. In some embodiments, the inventive apparatus includes 11) a control means for independently controlling the stations of the laser focal lens, capillary mount, collection lens and detector to prevent any mechanical cross-talk from one stage to the others that may adversely affect the resulting data.

Briefly, therefore, the invention is directed to a method of detecting a pteridine compound concentration in a biological sample obtained from a mammal, the method comprising treating the biological sample with an oxidizing agent in a concentration sufficient such that at least about 90 wt % of said concentration of pteridine compound in the biological sample is in its fully oxidized state; subjecting the sample to capillary electrophoresis using laser-induced fluorescence (CE-LIF) to cause the oxidized portion of said concentration of said pteridine compound to emit fluorescent light; detecting the emitted fluorescence light; and analyzing the emitted fluorescence light to determine the concentration of the pteridine compound in the biological sample.

The invention is also directed to a method for screening for cancer in a mammal, the method comprising quantitatively measuring a concentration of oncopterin (N2-(3-aminopropyl) biopterin) in a biological sample from the mammal by capillary electrophoresis-lased induced fluorescence; and comparing the concentration of oncopterin (N2-(3-aminopropyl) biopterin) in the sample with the concentration of oncopterin (N2-(3-aminopropyl) biopterin) in a biological sample from a healthy mammal of the same species to determine whether the concentrations of oncopterin (N2-(3-aminopropyl) biopterin) is significantly elevated or decreased.

In a further aspect, the invention is directed to an apparatus for determining a concentration of pteridine in a biological sample, the apparatus comprising an excitation source emitting non-polarized laser light capable of inducing the pteridine to emit fluorescent light and having a power output of at least about 1 mW; an electrophoresis capillary having a detection window and being capable of separating the pteridine from other components of the biological sample; a first optical system for focusing the non-polarized laser light onto the detection window of the capillary, wherein the first optical system comprises a focal lens; a light collection device for collecting fluorescent light emitted from the pteridine in the biological sample; and a second optical system for magnifying fluorescent light emitted from the pteridine and for focusing the magnified fluorescent light onto the light collection device, wherein the second optical system comprises a confocal lens having a magnification greater than 10× and a physical iris diaphragm.

Other objects and features of the invention will be in part apparent and in part pointed out hereinafter.

BRIEF DESCRIPTION OF THE DRAWINGS

Corresponding reference characters indicate corresponding parts throughout the drawings.

DESCRIPTION OF THE EMBODIMENT(S) OF THE INVENTION

Figure 1:
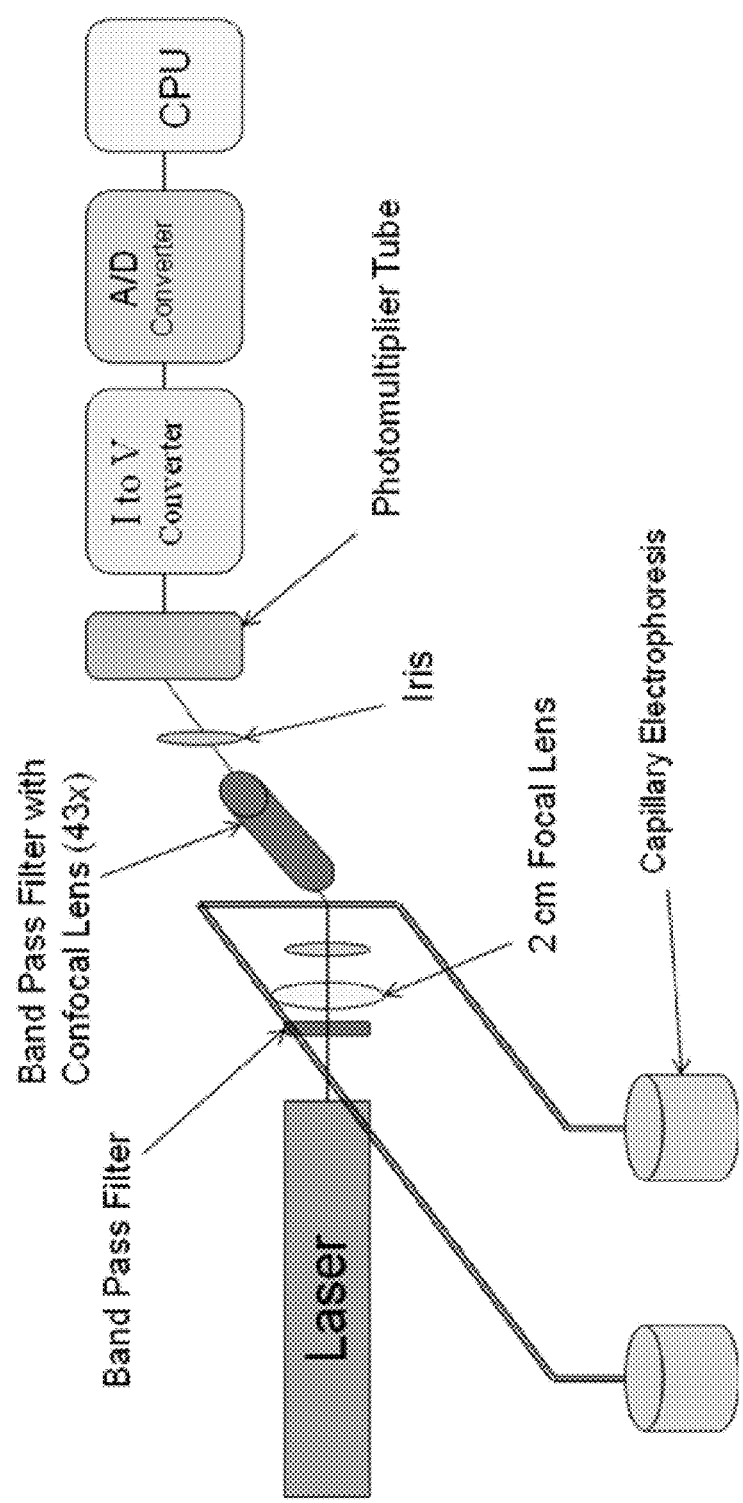
FIG. 1 is a schematic design of the capillary electrophoresis with laser induced fluorescence detection (CE-LIF) apparatus of the present invention.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

The present invention provides a cancer screening method for detecting pteridine levels in a biological sample, e.g., a urine sample, using capillary electrophoresis-laser induced fluorescence (CE-LIF) technology.

The major pteridines molecules that are detected in accordance with this invention are one or more from among 6,7-dimethylpterin, 6-biopterin, D-(+)-neopterin, 6-hydroxymethylpterin, pterin, isoxanthopterin, xanthopterin, pterin-6-carboxylic acid, and oncopterin ((N²-(3-aminopropyl) biopterin). The structures of these pteridines are shown in the following Table 1.

TABLE 1

| Pteridine | Structure |
|---|---|
| 6,7-dimethylpterin | 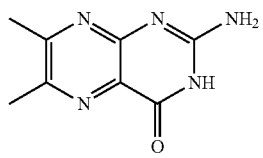 |
| 6-biopterin | 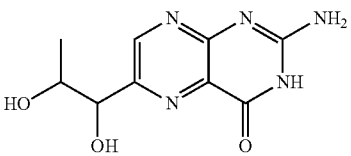 [SMILES: CC(O)C(O)c1cnc2nc(N)[nH]c(=O)c2n1] |
| D-(+)-neopterin | 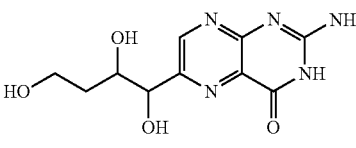 |
| 6-hydroxymethylpterin | 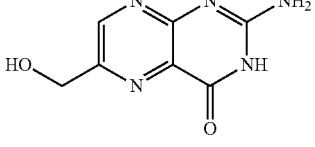 |
| Pterin | 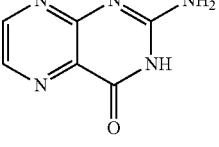 |
| Isoxanthopterin | 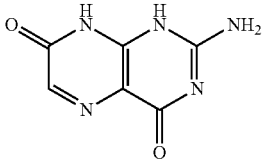 [SMILES: Nc1nc(=O)c2ncc(=O)[nH]c2[nH]1] |
| Xanthopterin | 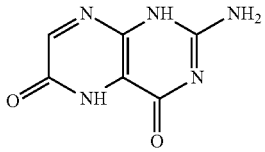 [SMILES: Nc1nc(=O)c2[nH]c(=O)cnc2[nH]1] |
| pterin-6-carboxylic acid | 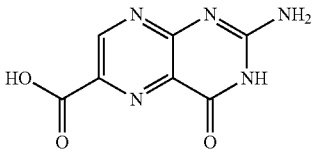 [SMILES: Nc1nc2ncc(C(=O)O)nc2c(=O)[nH]1] |
| oncopterin ((N²-(3-aminopropyl) biopterin) | 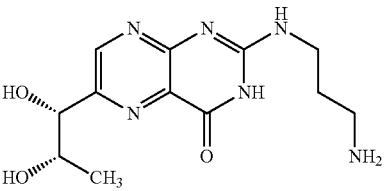 [SMILES: C[C@H](O)[C@H](O)c1cnc2nc(NCCCN)[nH]c(=O)c2n1] |

As shown in Table 1, the above listed molecules all contain a pterin base with a variety of functional groups that can be bonded to the C6 carbon of the bi-cyclic pterin molecule forming the pteridine of interest.

In general, the method of the present invention involves the following steps:

1) Preparing a urine sample for analysis;

2) Separating the pteridines in the prepared sample by capillary electrophoresis (CE); and 3) detecting pteridine levels in the sample with laser induced fluorescence (LIF).

Sample preparation involves oxidation of the pteridines in the biological sample. The sample is additionally pH adjusted by alkalinizing the sample. The sample may be centrifuged and diluted prior to separation by capillary electrophoresis.

The present invention is further directed to an apparatus that may be used to detect pteridine levels in a biological sample, e.g., a urine sample, by capillary electrophoresis-laser induced fluorescence (CE-LIF).

I. Sample Preparation

According to some embodiments of the method of the present invention, a biological sample, e.g., a urine sample, which is known to contain pteridines is prepared for analysis via capillary electrophoresis-laser induced fluorescence (CE-LIF).

Pteridines in biological samples generally exist in three oxidative states. The most reduced biological state is the tetrahydropteridin form. According to the nomenclature in the art, a tetrahydropteridin form of biopterin, for example, is referred to as tetrahydrobiopterin and written as $H_4B$ in shorthand. An intermediate reduced biological state is the dihydropteridin form. According to the nomenclature in the art, a dihydropteridin form of biopterin is referred to as dihydrobiopterin and written as $H_2B$ in shorthand. Accordingly, reduced compounds are indicated by the prefixes 'dihydro'-, 'tetrahydro'-, etc., with numerals indicating the positions of the additional hydrogen atoms, if known. A tetrahydro-compound is assumed to be substituted in the 5, 6, 7, and 8 positions, and a dihydro-compound is assumed to be substituted in the 7 and 8 positions, unless otherwise indicated:

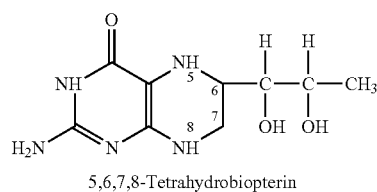 [SMILES: CC(O)C(O)C1CNc2nc(N)[nH]c(=O)c2N1]

5,6,7,8-Tetrahydrobiopterin

Biological samples may comprise pteridines in a fully oxidized state. According to the nomenclature in the art, the fully oxidized form of biopterin is simply referred to as biopterin and written as B in shorthand. The structures of biopterin in its fully oxidized state, as the dihydrobiopterin intermediate reduced state, and the fully reduced tetrahydrobiopterin, are shown below:

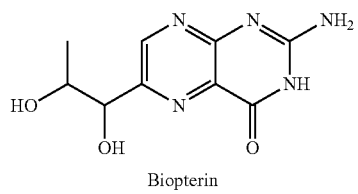

Biopterin

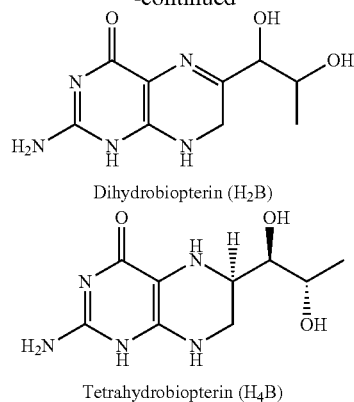

Dihydrobiopterin ($H_2B$)

Tetrahydrobiopterin ($H_4B$)

In accordance with this invention, pteridines in the biological sample, e.g., urine sample, are oxidized to their fully oxidized state. It has been discovered that fully oxidized pteridines produce a simpler sample matrix with less background interference, and are easily prepared and quantified. The oxidation treatment is sufficient to quantitatively oxidize pteridines that may be in their lower (e.g., dihydro or tetrahydro) redox state in the sample to their fully oxidized state. In one aspect, the oxidation treatment is sufficient to oxidize tetrahydro and dihydropteridines into the fully oxidized state such that the concentration of one or more pteridine compounds being analyzed that exist in the sample in their fully oxidized state comprise at least about 90 wt % (or 95 wt %, or 99 wt %, or 99.9 wt %) of the total of such pteridines in the sample. Stated another way, the total concentration of the pteridine compounds being analyzed that exist in the sample in the tetrahydro or dihydro (or other) reduced states is less than about 10 wt % of the total of such pteridine compounds in the sample. Preferably, oxidative treatment is sufficient to oxidize the pteridines being analyzed such that at least about 95 wt % of the total of such pteridines in the sample are in the fully oxidized form (e.g., less than about 5 wt % of such pteridines are in the, e.g., tetrahydro or dihydro, reduced states), even more preferably at least about 99 wt % of the total of such pteridines in the sample are in the fully oxidized form, such as at least about 99.9 wt % of the total of such pteridines are in the fully oxidized form. It has been discovered that the best results are achieved for early cancer screening if in accordance with this invention all or essentially all of the pteridines are fully oxidized, by which it is meant 100 wt % or nearly 100% of the pteridine concentration, and it is meant of all the several known pteridine species.

Accordingly, the invention involves treating the biological sample with an oxidizing agent in a concentration sufficient such that at least about 90 wt % of the concentration of a pteridine compound in the biological sample is in its fully oxidized state, and that pteridine compound concentration is then detected. The pteridine compound which is oxidized to its fully oxidized state is selected from the group consisting of 6,7-dimethylpterin, 6-biopterin, D-(+)-neopterin, 6-hydroxymethylpterin, pterin, isoxanthopterin, xanthopterin, pterin-6-carboxylic acid, oncopterin (($N^2$-(3-aminopropyl) biopterin), and two or more of said compounds. In other words, in various embodiments one might focus on only one such pteridine compound; and in other embodiments one might focus on several or all such pteridine compounds. For best results, all of these eight compounds are fully oxidized. Also, in this sense it is understood that each of these eight listed compounds may exist in the sample initially in a less oxidized state having a different name. So, for example, when the process is described as oxidizing at least about 90 wt % of the biopterine concentration to its fully oxidized state, it is to be understood that it is described this way for clarity purposes, and this encompasses and requires oxidizing at least about 90 wt % of the concentration of all the lower oxidized forms thereof (e.g., tetrahydropteridine and dihydropteridine) to biopterine. The description therefore encompasses oxidizing at least about 90 wt % (95 wt %, or 99 wt %) of the lower oxidized forms of 6,7-dimethylpterin to the fully oxidized state; oxidizing at least about 90 wt % (95 wt %, or 99 wt %) of the lower oxidized forms of 6-biopterin to the fully oxidized state; oxidizing at least about 90 wt % (95 wt %, or 99 wt %) of the lower oxidized forms of D-(+)-neopterin to the fully oxidized state; oxidizing at least about 90 wt % (95 wt %, or 99 wt %) of the lower oxidized forms of pterin to the fully oxidized state; oxidizing at least about 90 wt % (95 wt %, or 99 wt %) of the lower oxidized forms of isoxanthopterin to the fully oxidized state; oxidizing at least about 90 wt % (95 wt %, or 99 wt %) of the lower oxidized forms of xanthopterin to the fully oxidized state; oxidizing at least about 90 wt % (95 wt %, or 99 wt %) of the lower oxidized forms of pterin-6-carboxylic acid to the fully oxidized state; oxidizing at least about 90 wt % (95 wt %, or 99 wt %) of the lower oxidized forms of oncopterin (($N^2$-(3-aminopropyl) biopterin) to the fully oxidized state.

The pteridines in the biological sample, e.g., urine sample, may be oxidized by a variety of oxidation reagents, for example, iodine, peroxide, persulfate, nitrates, chlorites, permanganate, or iron(III) chloride. Oxidation of the pteridines to their fully oxidized state is preferably carried out by exposing the biological sample containing pteridines to iodine. In some embodiments, the oxidation solution contains elemental iodine and an iodine salt. Oxidation methods are disclosed in Trehan (J. Clin. Biochem. and Nut., 14, 195-203, 1993), Sawada (Clin. Chim. Acta, 138, 275-282, 1984), and Goldberg (J. Vet. Med. A., 34, 481-486, 1987 and Pteridines, vol 1, 29-35, 1989).

In preferred embodiments, the oxidizing solution comprises 4.0% (w/v) potassium iodide and 2.0% (w/v) iodine. The oxidizing solution may be prepared in bulk and stored in a dark container and sealed within a secondary container (such as aluminum foil) to avoid photo degradation of iodine. In preferred embodiments, the pteridines are oxidized by contacting the biological sample containing pteridines with a composition comprising 4.0% (w/v) potassium iodide and 2.0% (w/v) iodine in a concentration that is sufficient to quantitatively oxidize the pteridines that exist in the sample in a reduced form. In preferred embodiments, the iodine concentration is present in a stoichiometric excess over the estimated concentration of pteridine that is in a reduced form. Preferably, the molar ratio of iodine to the estimated concentration of pteridine in the sample that is in a reduced form is at least about 1:1, such as at least about 2:1, preferably at least about 4:1.

In some embodiments, oxidation of the pteridines in the biological sample occurs under alkaline conditions. The pH of the biological sample is adjusted to an alkaline condition because pteridines are only sparingly soluble or insoluble in acidic pH. The pH of the biological sample may be adjusted to an alkaline pH between about 7.5 and about 11, preferably between about 8 and about 10, even more preferably between about 9 and 9.8. Standard alkaline adjustment agents may be used, such as sodium hydroxide, potassium hydroxide, and amines such as tetramethylammonium hydroxide.

In general, oxidation occurs to an extent sufficient to quantitatively oxidize the pteridines in the sample to their fully oxidized state after about 30 minutes exposure to the oxidizing agent. Due to the potential photo activity of pteridines and urine, oxidation preferably occurs in dark environments.

After oxidation and alkalinization, the sample is centrifuged. A biological sample that is subjected to alkalinization and oxidation generally contains insoluble material. The sample is centrifuged for a duration and centrifugal force sufficient to separate the insoluble materials into a solid plug on the bottom of the vessel. The liquid is separated from the solid. The supernatant liquid is then diluted with sample buffer generally at a ratio of at least 1 part sample to 1 part sample buffer, but the dilution may be greater if the pteridine concentration is too high for the detector.

II. Capillary Electrophoresis

Capillary electrophoresis (CE) generally involves the application of high voltages across buffer-filled capillaries to achieve separations by their charge and frictional forces and hydrodynamic radius. Operation of a high-performance capillary electrophoresis (HPCE) system involves application of a high voltage across a narrow bore capillary. The separation of compounds by capillary electrophoresis is dependent on the differential migration of analytes in an applied electric field. Voltages for establishing the electric field generally vary from between about 10 kV and about 30 kV.

The capillaries used are normally fused silica capillaries covered with an opaque external polymer protective coating to give them increased mechanical strength. A small portion of this coating is removed to form a window for detection purposes. Removal of the polymer protective coating renders the capillary detection window transparent to visible light wavelengths and light wavelengths of the excitation source. The window is aligned in the optical center of the detector. Capillaries are typically between about 25 cm and about 200 cm long, preferably between 25 cm and 100 cm long. Preferably, the window is between about 15 cm and about 100 cm from the sample introduction point, thereby defining an effective length of the capillary of sufficient length to separate the compounds of interest. Capillary inner diameters may vary from about 25 micrometers to about 300 micrometers. In embodiments of the present invention, the capillary inner diameter is preferably between about 25 micrometers and about 200 micrometers. Successful separations have occurred in capillaries having internal diameters of 50 micrometers and 75 micrometers. On standard commercial high-performance capillary electrophoresis (HPCE) instruments, the capillary is typically held in a housing device as a cartridge to facilitate ease of capillary insertion into the instruction and to protect the delicate detection window area.

The capillary is filled with a buffer solution which conducts current through the inside of the capillary. The ends of the capillary are dipped into reservoirs filled with the buffer. Electrodes made of an inert material such as platinum are also inserted into the buffer reservoirs to complete the electrical circuit. Preferred operating buffers include tris(hydroxymethyl)aminomethane ("Tris"), 2-N-(morpholine)ethanesulfonic acid, N-(2-acetamido)iminodiacetic acid, piperazine-N,N'-bis(2-ethanesulfonic acid, N(2-acetamido)-2-aminoethanesulfonic acid, (2-aminoethyl)trimethylammonium chloride hydrochloride, N,N-bis(2-hydroxyethyl)-2-aminoethane sulfonic acid, N2-hydroxyethylpiperzine-N'-2-ethanesulfonic acid, N-tris(hydroxylmethyl)methylglycine, N—N-bis(2-hydroxyethyl)-glycine, 2-(N-cyclohexylamino) ethanesulfonic acid, and mixtures thereof.

In some embodiments, the running buffer is a Tris buffer in a concentration between about 0.05 M and about 0.2M, preferably about 0.1 M. The running buffer may additionally comprise borate, phosphate, or acetate in a concentration sufficient to carry a current, such as between about 0.01 M and about 0.15 M. Tris-borate is a commonly used running buffer.

The running buffer may additionally comprise a complexing agent, such as ethylenediamine tetraacetic acid. It has further been found that the concentration of EDTA in the buffer influences the separation of pteridines while in a free condition. Specifically, concentrations of up to about 2 mM EDTA enhances the separation of the two isomers, isoxanthopterin and xanthopterin.

The pH of the running buffer is generally between about 7.0 and about 12.0, preferably between about 8.0 and about 10.0, such as between about 9.0 and about 10.0. The running buffer is generally from 8.0 to 10 to assist in the systematic isolation of specific pteridines within the compounds of interest. Standard alkaline adjustment agents may be used, such as sodium hydroxide, potassium hydroxide, and amines such as tetramethylammonium hydroxide. The optimized condition for separating urinary pteridines uses a running buffer with pH of 9.63±0.02.

Temperature has also been found to influence the separation of pteridines due to the change of mobility of the pteridines at various temperatures. The temperature of the pteridines during separation therefore should be in the range of from about 18° C. to 30° C., with from about 22° C. to 25° C. being preferred. The temperature may be regulated using a cooling system to counteract Joule heating caused by the resistance of the voltage through the electrolyte system. Cooler systems that effectively counteract Joule heating are preferred since the analyte peaks are sharper and more resolved.

The electrophoretic separation of pteridines in the biological sample begins with sample injection. The sample is prepared, e.g., oxidized and alkalinized, as described above and injected into the capillary via gravimetric injection, electrokinetic injection, pressure, or suction. Even though electrokinetic injections can provide an on-line concentration of analytes at low concentrations, it is a very selective injection technique and the amount of analyte injected is dependent on the electro mobility of the analyte, which makes the injection biased toward analytes having high electromobilities, thereby overweighting the concentrations thereof in the analyzed sample. Relatively, gravimetric injection is a less biased technique, where a true composition of the sample may be observed at the expense of a more diluted injection. To accomplish gravimetric injection, the sample is raised higher than the waste reservoir. The sample injection end of the capillary is placed into the sample vial and through capillary and siphoning action, the sample is introduced. Experimental results indicate that injection for 10 sec at a height of 17.5 cm introduced roughly 5-7 nL of sample.

In preferred embodiments, separation of pteridines from the sample occurs at electrophoretic potential (EP) in a range between about 20 kV and about 30 kV, such as between 24 and 26 kV. In a capillary having an effective distance between the sample injection point and the detection window between about 20 cm and about 40 cm, effective separation of pteridines in a biological sample can be achieved in 10 to 20 minutes. Empirical results to date indicate that separation efficiency of greater than 100,000 theoretical plates may be achieved using the capillary electrophoretic separation method of the present invention.

III. Laser Induced Fluorescence

In the method of the present invention, the electrophoretically separated pteridines are detected via lased induced fluorescence. The fluorescence produced by the sample is isolated and plotted with respect to time to form an electropherogram comprising distinct peaks representing the migration time of each pteridine in the sample. FIG. 1 is a schematic design detailing the optical setup of the apparatus according to one embodiment of the invention.

In general, LIF comprises irradiating the pteridine containing running buffer with radiation within the wavelength range between 270 nm and 450 nm, such as between about 270 nm and about 350 nm or between about 300 nm and about 450 nm, to induce fluorescence of the pteridines when a plug of a particular pteridine passes through the detection window. In some embodiments, the excitation source for Laser Induced Fluorescence (LIF) is a helium-cadmium laser operating in the range of about 320 to 330 nm, with about 325 nm being most preferred. One such laser is the Melles Griot Omnichrome Series-74, 325 nm laser (HeCd laser, 35 mW power, Carlsbad, Calif., USA). In some embodiments, the excitation source is a solid state laser in the wavelength range of about 300 nm to 450 nm, preferably about 350 nm. One such laser is an Inca brand laser available from Xiton Photonics GmbH of Kaiserlautern, Germany. In preferred embodiments, the excitation source has a power output of at least about 1 mW, at least about 10 mW, such as between about 1 mW and about 40 mW, between about 10 mW and about 40 mW, preferably between about 20 mW and about 25 mW. The excitation source may emit polarized or non-polarized light. In preferred embodiments, the excitation source emits non-polarized light. Non-polarized laser light is preferred since non-polarized light scatters less light upon impinging the capillary wall.

The CE-LIF apparatus comprises a filtration device capable of transmitting laser light of a desired wavelength. In general, the filtration device comprises a band pass filter that isolates and transmits the desired wavelength and attenuates all other wavelengths. In some preferred embodiments, the desired laser wavelength is 325 nm. A band pass filter suitable for the apparatus of the present invention is a 325 nm bandpass filter (Ealing, Holliston, Mass.; model UG-11). Several other types of band pass filters are available from Thorlaps of Newton, N.J., for example part number FL355-10 (laser line filter, CWL=355=/1 2 nam, FWHM-10=/-2 nm; family: 0.1" UV laser line filters). Ultraviolet scan data reveal that some pteridines absorb from about 200 to about 360 nm, with a $\Lambda_{max}$ around 350-360 for most. The excitation wavelengths of interest in the present method are therefore in the range of about 300 to about 450 nm.

The CE-LIF apparatus comprises an optical system for focusing the filtered, non-polarized laser onto the detection window of the capillary, the pathway by which the intended sample is separated and exposed to the filtered, non-polarized laser via a detection window on the capillary. The optical system comprises a focal length. Preferably, the focal length is as short as possible to reduce the amount of scatter or stray layer. In preferred embodiments, the optical system comprises, for example, a 2.0 cm focal length lens.

The high powered laser may have substantial scatter light. In view thereof, the CE-LIF apparatus preferably comprises an optical iris diaphragm positioned between the focal lens and the detection window of the capillary. The optical iris is positioned to cut off scatter light from the laser. A currently preferred iris is a 25 mm (outer diameter) High Performance Zero Aperture Series Iris Diaphragm available from Edmund Optics of Barrington, N.J. The iris is not narrowly critical to carrying out the invention; it reduces background noise to make the analysis more sensitive. It should be large enough to block all of the potential background and scattered light and close sufficiently to make the effective field of view small enough to allow only the width of the laser or emitting fluorescence through.

The CE-LIF apparatus comprises a sample holder with a detection window that facilitates the mounting of an electrophoresis capillary.

The CE-LIF apparatus comprises a capillary electrophoresis device as described above that is capable of separating the specific compounds of interest (pteridines) within the biological sample and delivering the sample to the detection window of the capillary mounted within the sample holder.

The CE-LIF apparatus preferably comprises a confocal lens having greater than 10× magnification placed in the range of 45 to 90 degrees (90 degrees being preferred) from the laser path to collect and focus fluorescence emission from the sample. In preferred embodiments, the confocal lens has greater than 20× magnification, greater than 30× magnification, or even greater than 40× magnification, such as 43× magnification. An exemplary confocal lens is available from Bausch and Lomb, 0.6 NA, 40×.

The CE-LIF apparatus preferably comprises a second filtration means for filtering fluorescence generated by impurities and other sources of fluorescence. The second filtration device is used to transmit fluorescence from pteridines while blocking fluorescence from non-pteridine sources. The second filtration means may be a bandpass filter designed to transmit pteridine fluorescence. The wavelengths transmitted are generally between 400 and 539 nm. Such a bandpass filter is available from Ealing, model 35-532.

The CE-LIF apparatus preferably comprises a physical optical iris diaphragm located between the bandpass filter/confocal lens and the fluorescent light collection device. The iris diaphragm removes any scattering either from the filtered non-polarized laser or from any fluorescence generated by the device. This iris is typically the same as the optical iris diaphragm positioned between the focal lens and the detection window of the capillary.

The CE-LIF apparatus comprises a detection means for detecting the filtered fluorescence emission generated by the pteridines in the samples of interest. A preferred light detection means is a photomultiplier tube, which is an extremely sensitive detector of light in the ultraviolet, visible, and near-infrared ranges of the electromagnetic spectrum. A commercially available PMT is a Hammatsu PMT, Type R928, No. IG6957.

The current signal from the fluorescent light detection device is preferably converted to a voltage via a current to voltage (I to V) converter, which communicates the raw output of electrons produced in the fluorescent light detection device produced by fluorescence from the compounds of interest undergoing fluorescent decay to the digital input of the device collecting the output.

The CE-LIF apparatus preferably comprises a control means for independently controlling the stations of the laser focal lens, capillary mount, collection lens and detector to prevent any mechanical cross-talk from one stage to the others that may adversely affect the resulting data.

The combination of a physical optical iris diaphragm placed between the focal lens and the capillary detection window, a high magnification confocal lens, and a physical optical iris diaphragm placed between the confocal lens and the light collection device provides an extremely stable baseline, which in turn yields high signal to noise ratios (S/N) and low limits of detection. According to some empirical results, the baseline is less than 1 mV, which enables low limits of detection. The limits of detection reported in the below examples were at S/N=5.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

Having described the invention in detail, it will be apparent that modifications and variations are possible without departing from the scope of the invention defined in the appended claims.

EXAMPLES

The following non-limiting examples are provided to further illustrate the present invention.

Example 1

The following example describes a high performance capillary electrophoresis (HPCE) separation of pteridines in a biological sample with laser-induced fluorescence (LIF) detection method (HPCE-LIF) for quantitative analysis of pteridines in urine samples. HPCE-LIF was used to investigate pteridine level patterns in 38 urine samples from a variety of cancer patients. Some types of cancer were not studied mainly due to the unavailability of urine samples and not the limitation of the technique. In order to assure that the pteridine levels represent the physiological concentration, the amount of pteridines was reported here as a ratio of pteridine to creatinine See Shi H., Ma Y., Ma Y. A Simple and Fast Method to Determine and Quantify Urinary Creatinine, Anal. Chim. Acta., 1995, 312, pp. 79-83.

Materials and Methods.

Chemicals.

Pteridine standard solutions of 6-biopterin, D-(+)-neopterin, pterin, isoxanthopterin, xanthopterin pteridine were purchased from Sigma-Aldrich (St. Louis, Mo.). Standard solutions of 6,7-dimethylpterin and 6-hydroxymethylpterin were purchased from Schircks Laboratories (Jona, Switzerland). Boric acid and Tris(hydroxymethyl)aminomethane were purchased from Sigma-Aldrich (St. Louis, Mo.). EDTA disodium salt, iodide, potassium iodine, sodium hydroxide and sodium phosphate dibasic were purchased from Fisher (Fair Lawn, N.J.). Ultrapure water was obtained using a Milli-Q Advantage® A10 and Millipore Elix® water purification system.

pH Measurement.

All pH measurements were performed on an Accumets® Excel XL-15 pH meter that was standardized using pH standards 4, 7, and 10 (Fisher Scientific™). Standard creatinine for creatinine analysis was purchased from Sigma-Aldrich® (Milwaukee, Wis.).

Buffer Preparation.

A 0.1 M Tris/0.1 M borate/2 mM EDTA running buffer was prepared and pH was adjusted to 9.63±0.02 using 2.0 M NaOH. A 50 mM aqueous solution of $Na_2HPO_4$ sample buffer was prepared and pH was adjusted to 7.70±0.02 using concentrated phosphoric acid. This was used to dilute both standards and samples. A 15 mM $KH_2PO_4$ solution was prepared and pH was adjusted to 6.4 using 1.0 M NaOH. This was used as the running buffer for creatinine analysis. The creatinine sample dilution buffer was prepared in exactly the same way as the running buffer except that 2% EDTA was present in sample dilution buffer. EDTA was used to complex the metal ions in the urine sample so that these ions would not form complexes with creatinine. All the buffers were filtered with a 0.45 µm membrane and degassed before use.

Standard Preparation.

To prepare pteridine standard solutions, 2 mg of pteridine standard was dissolved in a solution consisting of 0.3 mL of 1.0 M sodium hydroxide and 9.7 mL of sample buffer. A standard mixture was then prepared by combining equal-molar concentrations of each standard and diluted to a final concentration of $5.0 \times 10^{-5}$ M with the sample buffer. A dilution series of this stock solution was used to generate calibration curves. Standard creatinine stock solution was prepared by dissolving 50 mg creatinine into 50 mL sample dilution buffer to make the creatinine concentration 100 mg/dL. This standard stock solution was diluted to an appropriate concentration with the sample dilution buffer.

Oxidizing Solution Preparation.

The oxidizing solution consisted of 4.0% potassium iodide and 2.0% iodine (w/v). It was prepared by dissolving 0.6008 g of KI in 15 mL of Milli-Q water. Once the KI was dissolved, 0.3025 g of $I_2$ was added to the solution. The solution was then stirred (for about 1 h) until the $I_2$ was completely dissolved. The final solution was stored in an amber glass vial, and the cap was wrapped with Parafilm®. The vial was wrapped with aluminum foil to avoid photo degradation of the iodine.

Urine Sample Preparation.

Urine samples from cancer patients who did not undergo chemical or radiation therapy were obtained from Ellis Fischel Cancer Center, Columbia, Mo. The normal urine samples were collected from student volunteers at Missouri S&T who did not take any medications including vitamin supplements. The demographic distribution of cancer patients and normal subjects were mainly from nearby cities. The age distribution of cancer patients was from 26-70 y, and the range for normal subjects was 22-45 y. There was no dietary or exercise restriction performed among the control group or the cancer patients. The urine from the cancer patients represented breast (12), lung (9), colon (4), rectal (2), pancreatic (1), ovarian (3), non-Hodgkins lymphoma (4), esophageal (4), bladder (1), and kidney (1) cancers. All the samples were stored in a freezer at −80° C. Prior to analysis, the samples were removed from the freezer and brought to room temperature. A 1000 µL aliquot of urine sample was taken using a micropipette and placed in a 1.5 mL yellow microcentrifuge tube. Then 400 µL of the oxidizing solution and 100 µL of 2.0 M NaOH were added to the sample and mixed well. The sample mixture was incubated at 4° C. for 30 min and centrifuged at 5000 rpm for 20 min at 4° C. Then 500 µL of the supernatant was placed in a new vial, and 500 µL of sample buffer was added to it. It was mixed thoroughly and injected directly into the CE for analysis. Further dilutions were made in some samples.

Capillary Electrophoresis Laser Induced Fluorescence System (CE-LIF).

A home-built capillary electrophoresis LIF system was used for this study. A depiction of the device is provided in FIG. 1. A Melles Griot Omnichrome Series-74, 325 nm laser (HeCd laser, 35 mW power, Carlsbad, Calif., USA) was used for excitation. The stray and scattered light from the nonpolarized laser were removed using a 325 nm band-pass filter (Ealing, Holliston, Mass.; model UG-11). The laser was focused on the capillary window with a 2.0 cm focal length lens. Prior to impinging the detection window of the capillary, the laser beam passed through an iris, which remove scatter light from the laser. The first iris is positioned to provide the only pathway for light to enter the system, and the adjustment is the diameter of the opening. It is reduced to permit only the laser beam through. The second iris is positioned to provide the only pathway that fluorescence can get to the detector (PMT). Again, the adjustment is the diameter of the opening to reduce the effective field of view to only include light passing through the inner diameter of the capillary, which contains the sample and emits the fluorescence.

The fluorescence emission was collected by a microscopic objective and focused onto a R982 Hamamatsu photomultiplier tube (Bridgewater). The microscopic objection comprises a confocal lens having 40 or 43× magnification, which choice depended upon the experimental conditions. Background noise was minimized using a band-pass filter (400-539 nm, Ealing, model 35-532). A second iris is placed after the band pass filter and confocal lens (43× magnification) in order to reduce scatter light from the capillary. The resulting output current from the photomultiplier tube was converted to a voltage signal through a home-built current-to-voltage converter. The analog signal was then digitalized though a Logger Pro analog-to-digital converter (Verniers Software and Technology, Beaverton, Oreg.). The data were collected using Logger Pro 3.1 data collection software.

Creatinine Analysis.

Creatinine analysis was performed following a method that was previously developed in our group. See Shi H., Ma Y., Ma Y., A Simple and Fast Method to Determine and Quantify Urinary Creatinine, Anal. Chim. Acta., 1995, 312, pp. 79-83. A Beckman P/ACE capillary electrophoresis instrument equipped with ultraviolet absorbance was used for creatinine analysis. The detection wavelength was set at 214 nm. The capillary column (Polymicro Technologies, Phoenix, Ariz.) used was 60 cm×50 µm inner diameter fused silica tubing with an effective length of 35 cm. Electrophoresis was carried out at 20 kV. Urine samples were diluted with sample dilution buffer and directly injected into the HPCE column. The data were collected and processed by 32 Karat Software ver. 5.0 (Beckman, Inc.). Peaks were identified by both retention time and standard addition.

Pteridine Analysis Using CE-LIF.

A 70 cm length×50 µm inner diameter fused silica capillary (Polymicro Techniques, Phoenix, Ariz., USA) was used for separation. First, the new capillary was rinsed with 1.0 M NaOH for 15 min, followed by Milli-Q water for 5 min. Next, it was rinsed with 1 M HCl for 15 min, with Milli-Q water for 5 min, and finally with running buffer for 15 min. A 1 cm section of the polymer coating was burned off at 35 cm from the cathode end, forming the detection window and leaving an effective capillary length of 35 cm. Samples were injected into the capillary by the gravimetric method. Samples were injected 17.5 cm from the top of the sample to the instrument table with an injection time of 10 s. Electrophoresis was carried out at 26 kV (371 V/cm) for 20 min. After each injection, the capillary was regenerated by flushing with 0.2 M NaOH for 1 min, followed by a 2 min water rinse, and finally by a 2 min running buffer rinse. The individual pteridine peaks in the urine samples were identified by retention time comparisons and standard addition and obtained from the Logger Pro software.

Statistical Analysis.

Pteridine concentrations were determined by linear regression against experimentally generated calibration curves. The basic statistical information such as mean, variance, and pooled variance of each pteridine for both cancer and normal urine samples were calculated by Minitab Software. Statistical hypothesis testing was conducted to analyze the data. The null hypothesis was that the mean pteridine levels in cancer samples are lower than or equal to those in normal urine. The alternative hypothesis was that mean pteridine levels in cancer samples are higher than those in normal samples. The P values (last raw in Table 2) were calculated for all samples. The null hypothesis was rejected, and the results demonstrate that the alternative is significant at a 5% significance level if the P value ≤0.05.

TABLE 2

Basic Statistical Summaries of Each Pteridine for Cancer and Normal Urine Samples

| | Pteridine | | | |
|---|---|---|---|---|
| | 6,7-dimethyl pterin | 6-biopterin | 6-hydroxymethyl pterin | D-(+)-neopterin |
| Mean Cancer (n = 38) | 7.41E−04 | 8.96E−04 | 4.81E−04 | 1.14E−03 |
| Mean Normal (n = 17) | 2.79E−05 | 1.14E−04 | 4.83E−05 | 2.37E−04 |
| Variance Cancer | 8.81E−06 | 2.67E−06 | 9.20E−07 | 1.16E−05 |
| Variance Normal | 3.30E−09 | 1.14E−08 | 1.57E−09 | 1.20E−07 |
| Pooled Variance | 6.15E−06 | 1.87E−06 | 6.43E−07 | 8.16E−06 |
| t Stat | 0.986 | 1.958 | 1.849 | 1.079 |
| P (T <= t) one tail | 0.164 | 0.028 | 0.035 | 0.143 |

| | Pteridine | | | |
|---|---|---|---|---|
| | Pterin | Isoxantho pterin | Xantho pterin | Pterin-6-carboxylic acid |
| Mean Cancer (n = 38) | 6.00E−04 | 3.37E−02 | 5.59E−03 | 2.54E−04 |
| Mean Normal (n = 17) | 1.75E−04 | 1.06E−03 | 1.13E−03 | 1.25E−04 |
| Variance Cancer | 5.28E−07 | 1.10E−03 | 3.94E−05 | 9.109E−08 |
| Variance Normal | 2.93E−08 | 5.66E−07 | 1.47E−06 | 1.98E−08 |
| Pooled Variance | 3.78E−07 | 7.68E−04 | 2.79E−05 | 6.957E−08 |
| t Stat | 2.373 | 4.040 | 2.891 | 1.682 |
| P (T <= t) one tail | 0.011 | 8.67E−05 | 0.003 | 0.049 |

The standard mixture of 8 pteridines was first injected into the CE, and the elution order was obtained. The detection limit, linear equations and $R^2$ values are given in Table 3.

TABLE 3

Calibration Data for Each Pteridine

| Pteridine | Limit of Detection | Linear Equations of Calibration Curves | $R^2$ |
|---|---|---|---|
| 6,7-dimethyl pterin | $2.5 \times 10^{-10}$ | $y = 1.2383 \times 10^6 X + 0.9642$ | 0.9828 |
| 6-biopterin | $2.5 \times 10^{-10}$ | $y = 9.2704 \times 10^5 X + 0.3174$ | 0.9911 |
| 6-hydroxy-methyl pterin | $2.5 \times 10^{-10}$ | $y = 7.6386 \times 10^5 X + 0.3339$ | 0.9923 |
| D-(+)-neopterin | $2.5 \times 10^{-10}$ | $y = 9.2866 \times 10^5 X + 0.2902$ | 0.9947 |
| Pterin | $2.5 \times 10^{-10}$ | $y = 7.9057 \times 10^5 X + 0.3014$ | 0.9936 |
| Isoxanthopterin | $2.5 \times 10^{-10}$ | $y = 3.6299 \times 10^5 X + 0.0897$ | 0.9987 |
| Xanthopterin | $2.5 \times 10^{-10}$ | $y = 6.5796 \times 10^5 X + 0.0863$ | 0.9988 |
| Pterin-6-carboxylic acid | $4.72 \times 10^{-10}$ | $y = 1.6335 \times 10^6 X + 0.3788$ | 0.9988 |

Figure 2:
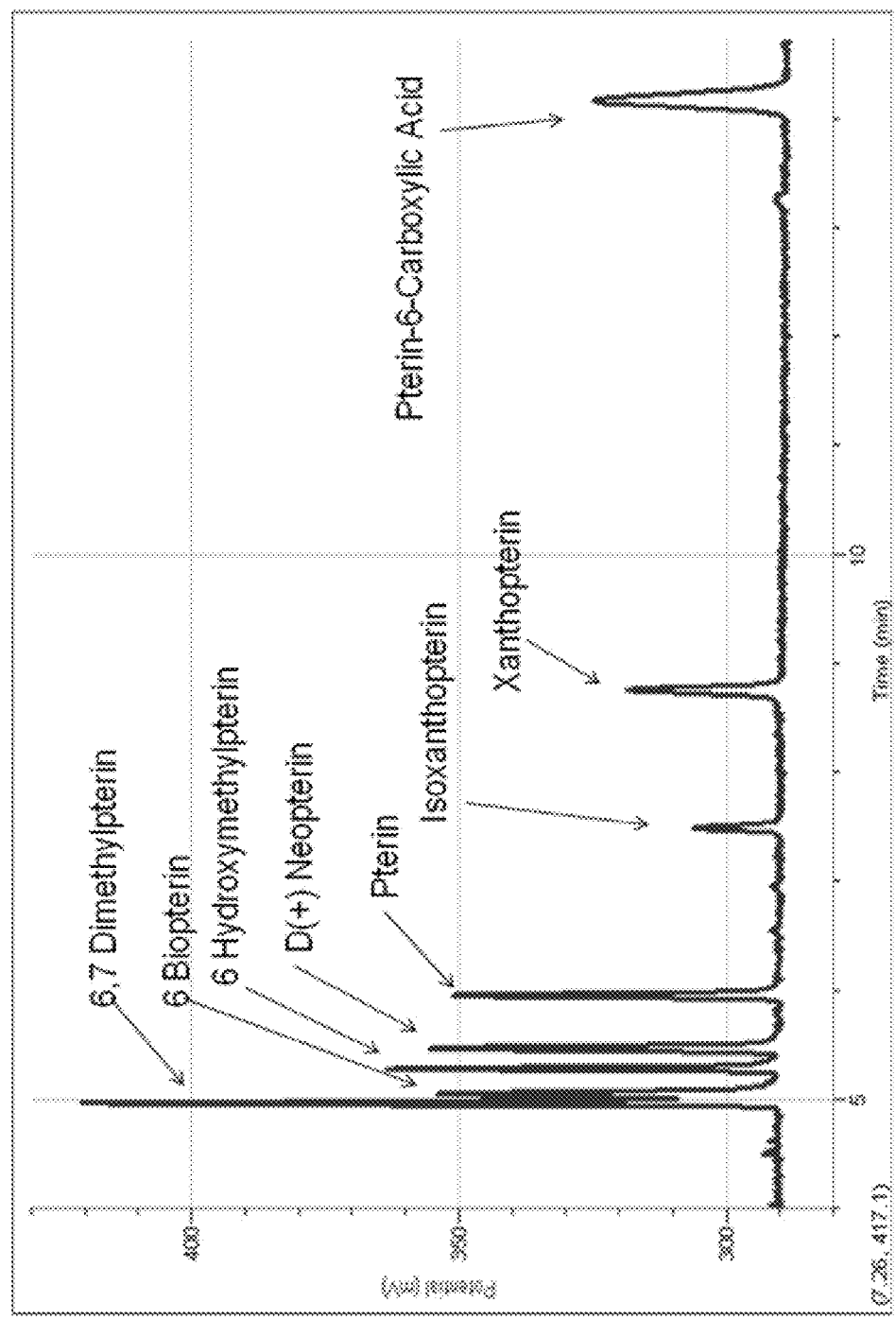
FIG. 2 is an electropherogram of the eight pteridine standards. The experimental conditions are described in the Example.

The electopherogram is shown in FIG. 2. The number of theoretical plates for the separation was determined to be 130,000. FIG. 2 showed that the 6,7-dimethylpterin eluted first and the pterin-6-carboxylic acid eluted last. FIGS. 3-12 show the box plots of various pteridines in samples from both cancer patients and healthy subjects. Creatinine calibration graph had a linear range from 0 to 20 mg/dL and $R^2$ was 0.9819. Creatinine levels in cancer patients and healthy subjects were shown in FIG. 13.

Figure 3:
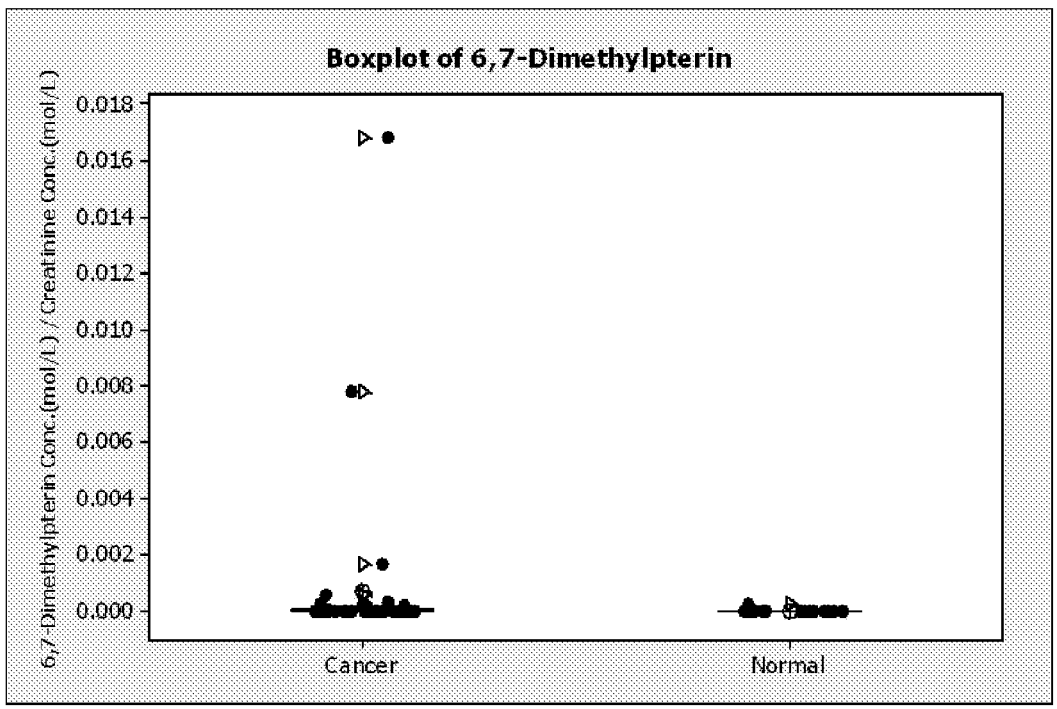
FIG. 3 is a box plot of 6,7-dimethylpterin levels in cancer urine samples (n=38) and normal urine samples (n=17).
Figure 4:
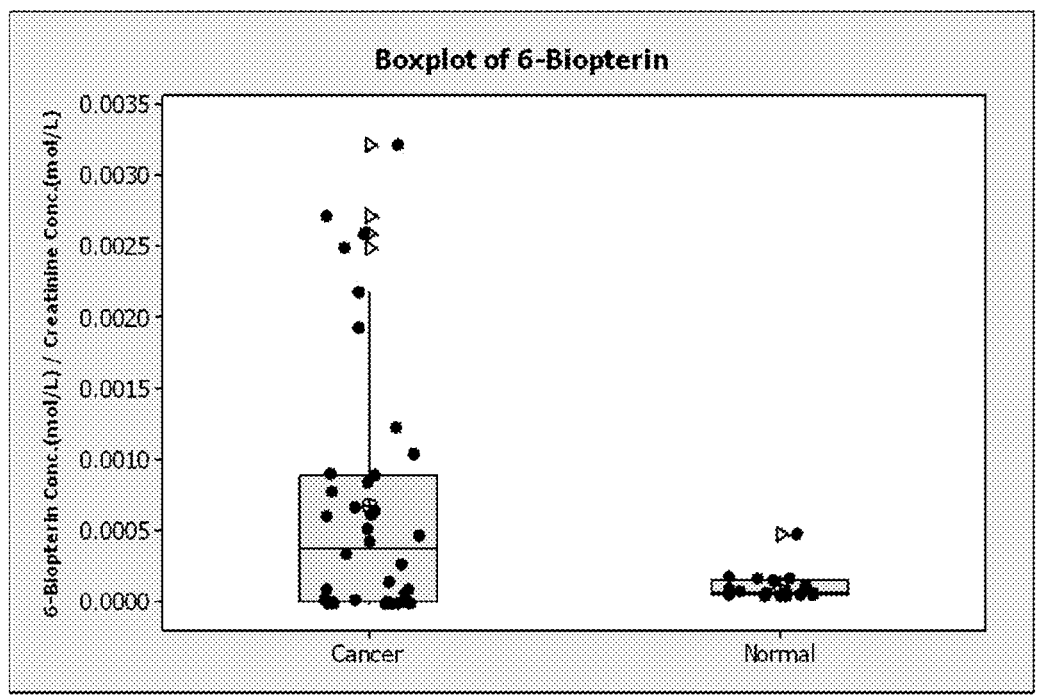
FIG. 4 is a box plot of 6-biopterin levels in cancer urine samples (n=38) and normal urine samples (n=17).
Figure 5:
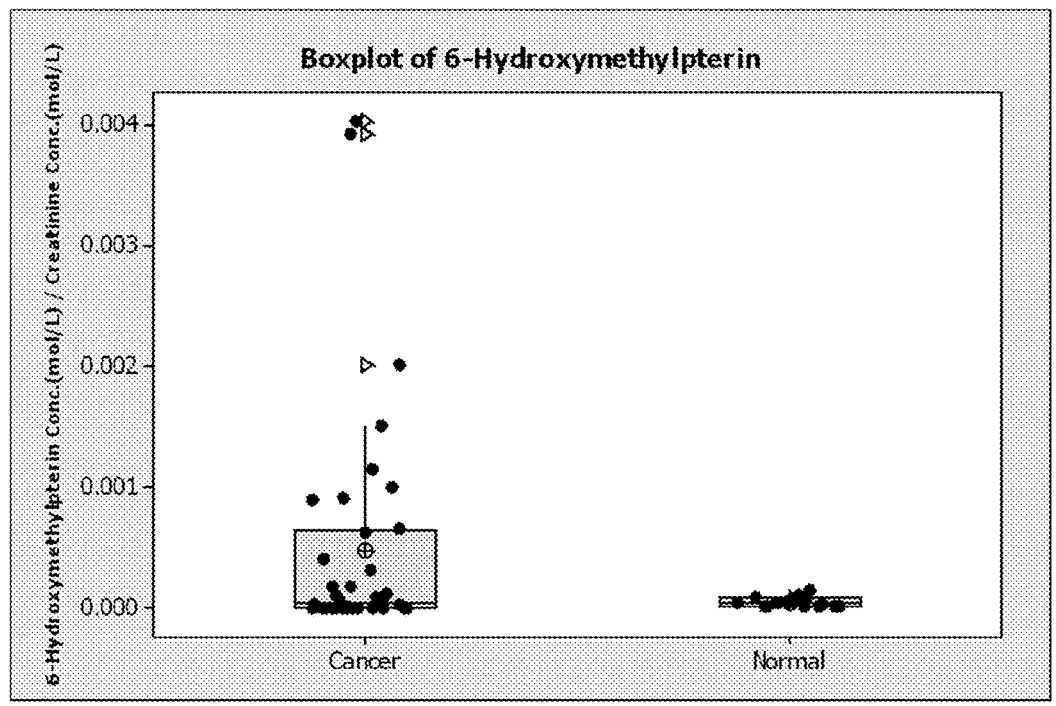
FIG. 5 is a box plot of 6-hydroxymethylpterin levels in cancer urine samples (n=38) and normal urine samples (n=17).
Figure 6:
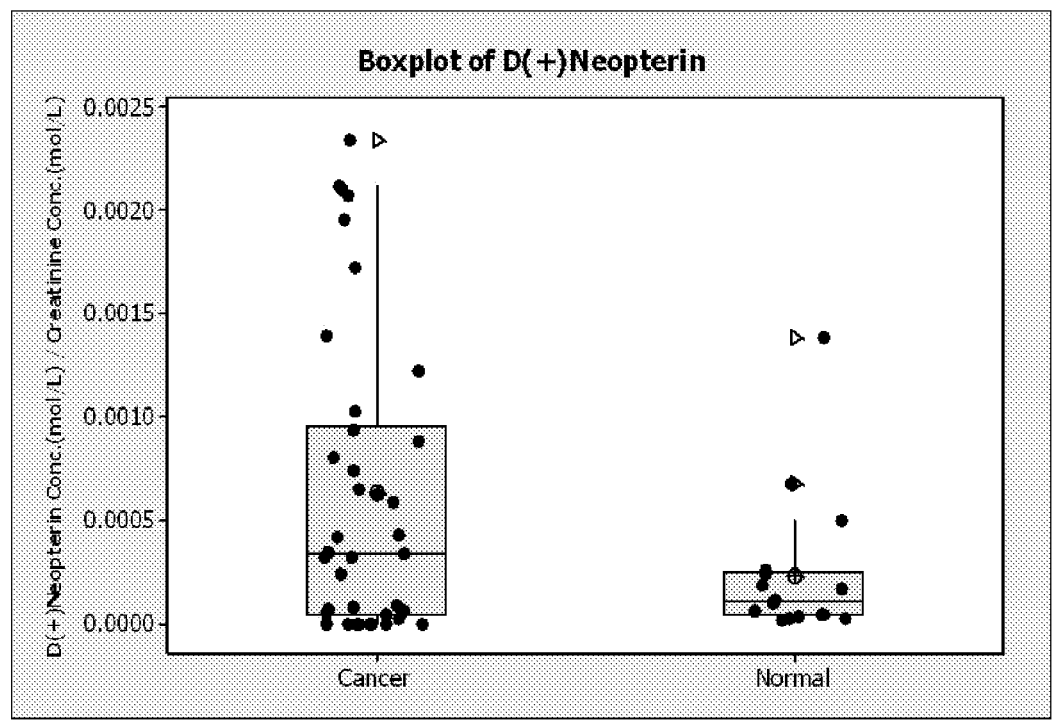
FIG. 6 is a box plot of D-(+)-neopterin levels in cancer urine samples (n=38) and normal urine samples (n=17).
Figure 7:
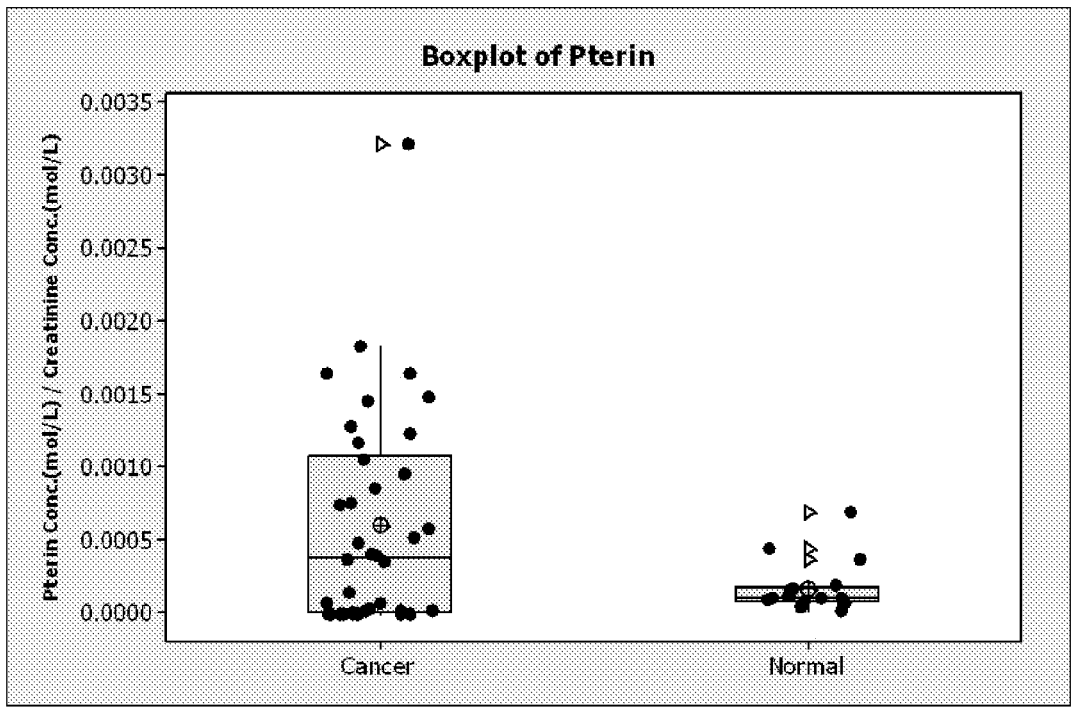
FIG. 7 is a box plot of pterin levels in cancer urine samples (n=38) and normal urine samples (n=17).
Figure 8:
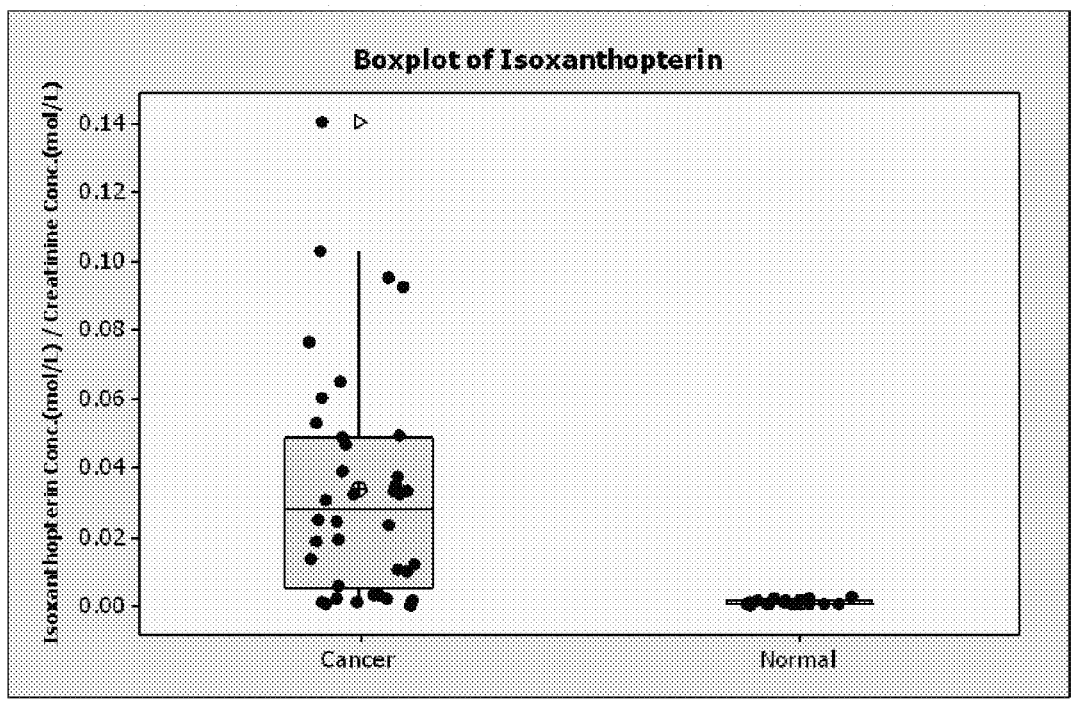
FIG. 8 is a box plot of isoxanthopterin levels in cancer urine samples (n=38) and normal urine samples (n=17).
Figure 9:
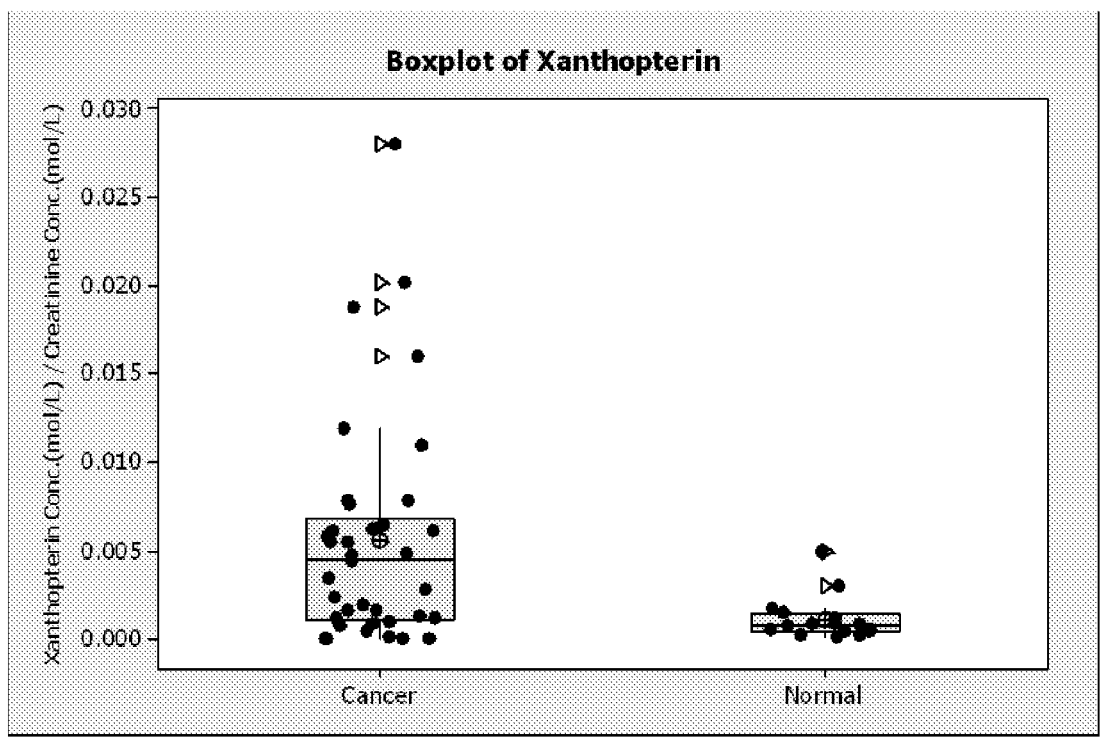
FIG. 9 is a box plot of xanthopterin levels in cancer urine samples (n=38) and normal urine samples (n=17).

Table 2 provided basic statistical information such as mean, variance, and pooled variance of each pteridine for both cancer and normal urine samples. The key objective of this work was to determine whether there is any significant difference between levels of pteridine in cancer urine samples and those in normal urine samples. FIG. 3 showed the box plot of 6,7-dimethylpterin. In the urine samples of cancer patients, 3 outliers are disregarded, there was no significant difference in levels of 6,7-dimethylpterin in cancer and normal samples. The P value of 6-biopterin was 0.028. So the mean value of 6-biopterin in the cancer samples was significantly greater than that in the normal samples (FIG. 4). FIG. 5 indicated that, even after the outliers were removed, the 6-hydroxymethylpterin level in cancer patients was higher than the normal (P=0.035). FIG. 6 showed that the D-(+)-neopterin level was higher in cancer patients than in normal subjects but P value was 0.143. Therefore, the D-(+)-neopterin level in cancer urine samples was not significantly greater than normal because D-(+)-neopterin variance was higher in cancer. The pterin levels in cancer were significantly higher than normal (P=0.011) (FIG. 7).

Figure 10:
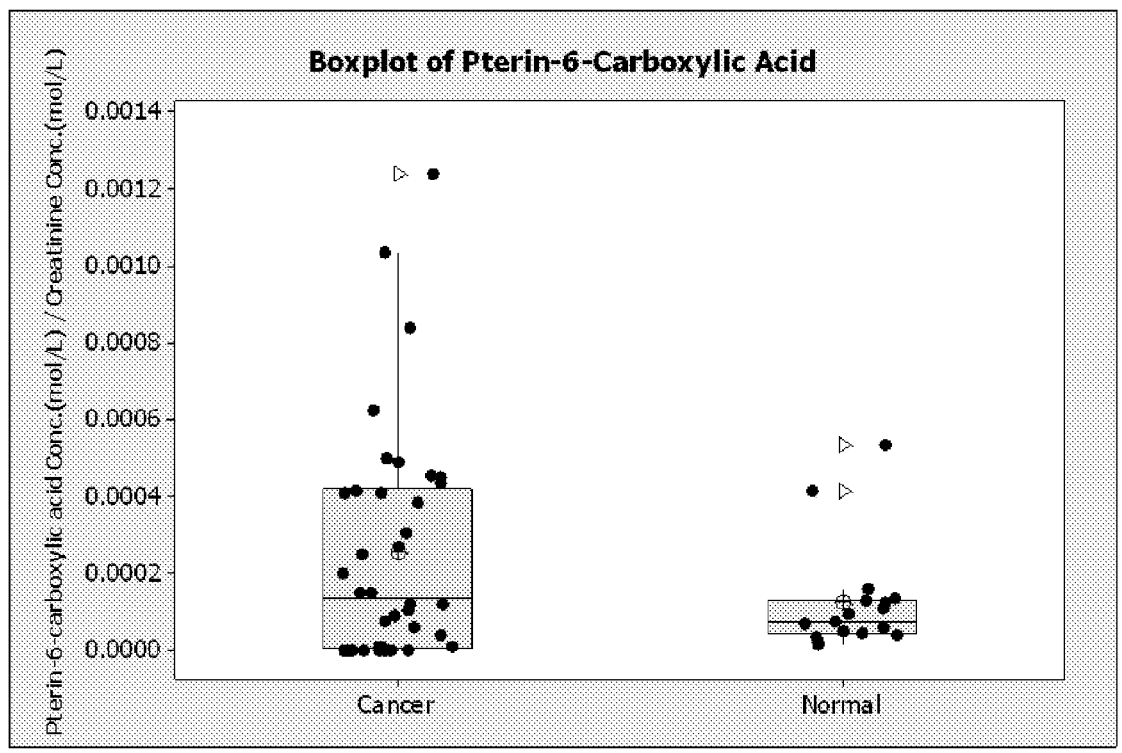
FIG. 10 is a box plot of xanthopterin levels in cancer urine samples (n=38) and normal urine samples (n=17).

In both cancer and normal urine samples, levels of xanthopterin and isoxanthopterin levels were higher than those of other pteridines, as indicated by the y axes of the box plots. The box plot for xanthopterin and isoxanthopterine (FIGS. 8 and 9) showed that levels in the cancer urine samples were much higher than in the normal urine samples (P=8.7×10$^{-5}$, and 2.8×10$^{-3}$, respectively). Han et al. previously showed that lower isoxanthopterin levels in cancer patients compared to the normal. See Han F., Huynh B. H., Shi H., Lin B., Ma Y., Pteridine Analysis in Urine by Capillary Electrophoresis Using Laser-Induced Fluorescence Detection, Anal. Chem., 1999, 71, pp. 1265-9. But they analyzed only 9 cancer patient urine samples and this may be due to outliers present in the data. The pterin-6-carboxylic acid was not significant (P=0.049) (FIG. 10).

Figure 11:
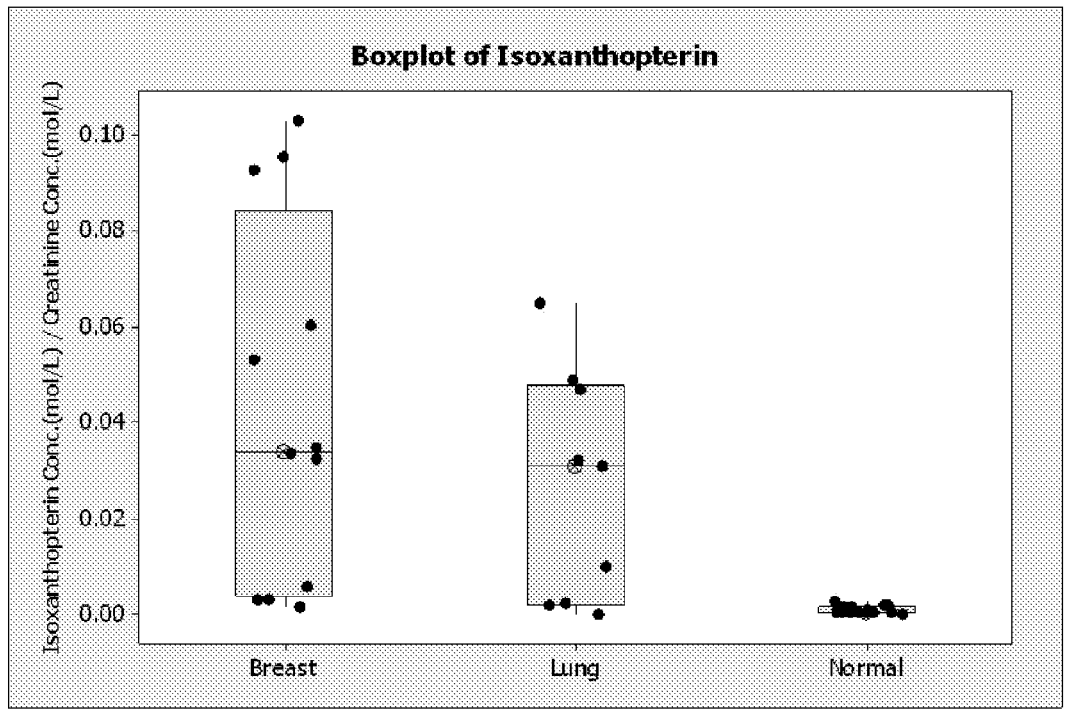
FIG. 11 is a box plot of isoxanthopterin levels in breast cancer urine samples (n=12), lung cancer urine samples (n=9), and normal urine samples (n=17).
Figure 12:
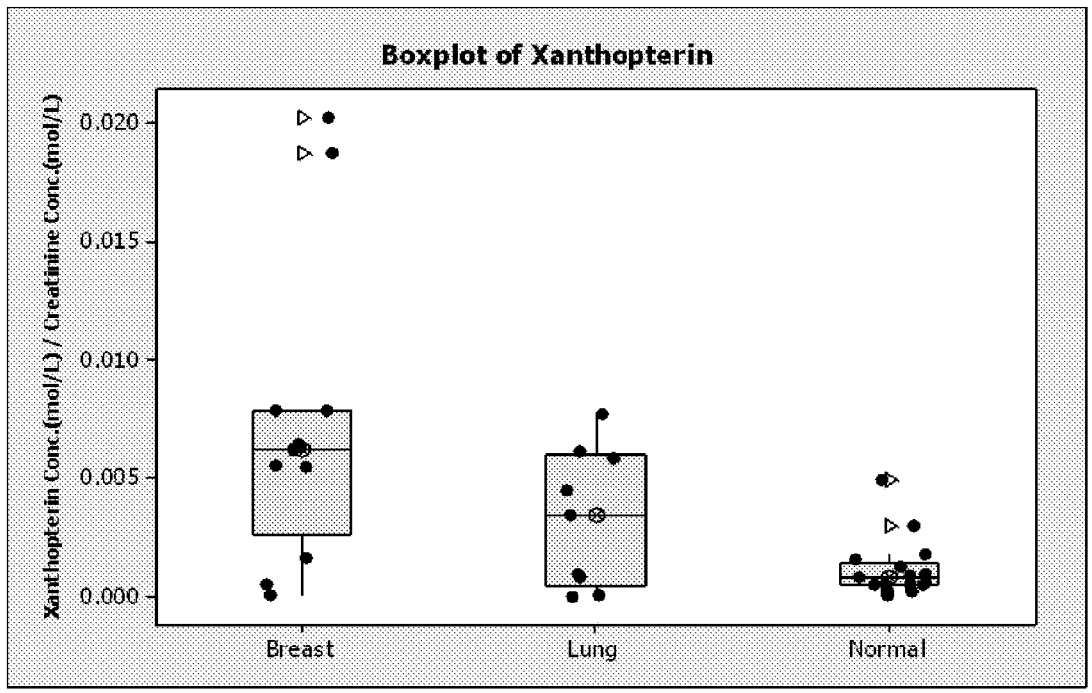
FIG. 12 is a box plot of xanthopterin levels in breast cancer urine samples (n=12), lung cancer urine samples (n=9), and normal urine samples (n=17).
Figure 13:
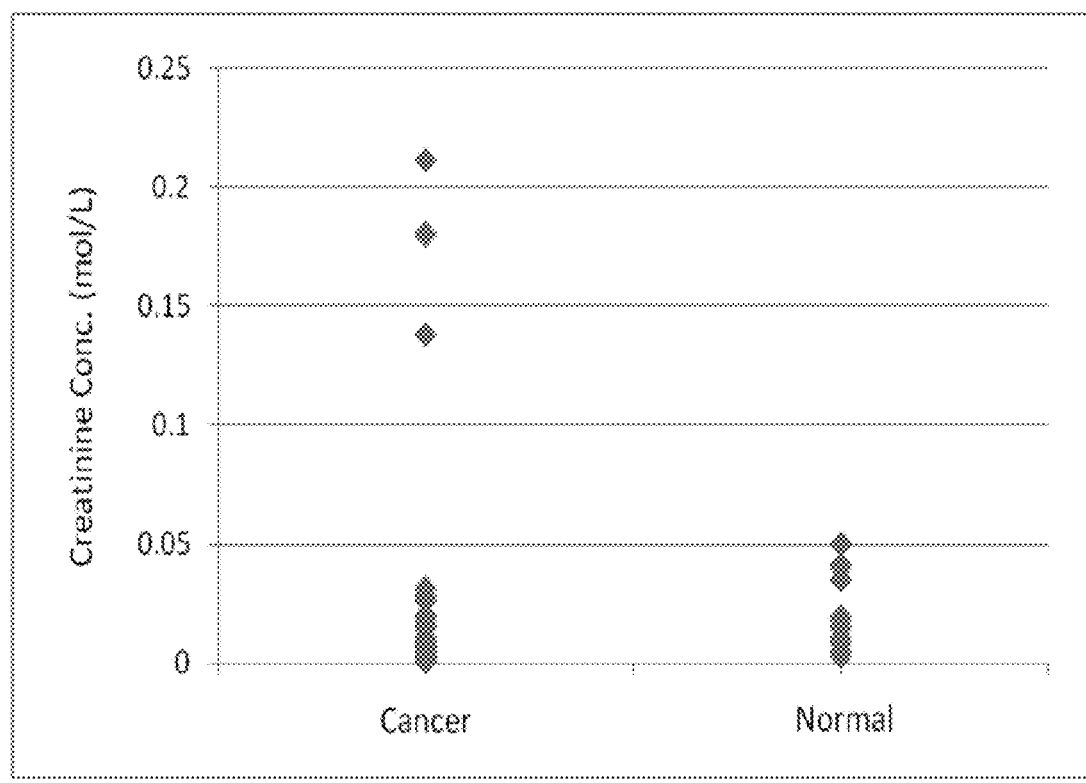
FIG. 13 is a scatter plot of creatinine levels in cancer urine samples (n=38) and normal urine samples (n=17).

A comparison of the P values of each pteridine demonstrates that xanthopterin and isoxanthopterin were much lower than those of the other pteridines. Thus, their levels in breast cancer (n=12) and lung cancer (n=9) urine samples were checked (FIGS. 11 and 12). Table 4 showed the P values calculated for various combinations. Xanthopterin and isoxanthopterin levels cannot be used to differentiate lung cancer from breast cancer. These biomarkers were significantly high in breast and lung vs. normal (P<0.05).

TABLE 4

Xanthopterin and isoxanthopterin P values for various combinations of lung cancer, breast cancer, and normal urine samples

| Pteridine | Combination | P |
|---|---|---|
| Xanthopterin | Lung Cancer v. Breast Cancer | 0.1311 |
| | Lung Cancer v. Normal | 8.51E−05 |
| | Breast Cancer v. Normal | 4.18E−05 |
| Isoxanthopterin | Lung Cancer v. Breast Cancer | 0.04898 |
| | Lung Cancer v. Normal | 0.000287 |
| | Breast Cancer v. Normal | 0.007288 |

This work analyzed 8 pteridines in urine samples from cancer patients and healthy subjects. Some pteridine levels in the urine samples of the cancer patients were higher than those of healthy subjects. More specifically, 6-biopterin, 6-hydroxymethylpterin, pterin, xanthopterin and isoxanthopterin levels in cancer samples were significantly higher than normal. Also, levels of xanthopterin and isoxanthopterin in both cancer patients and healthy subjects were higher than other pteridines. The foregoing demonstrates that the invention is effective for using pteridines as biomarkers for early cancer screening.

Example 2

Figure 14:
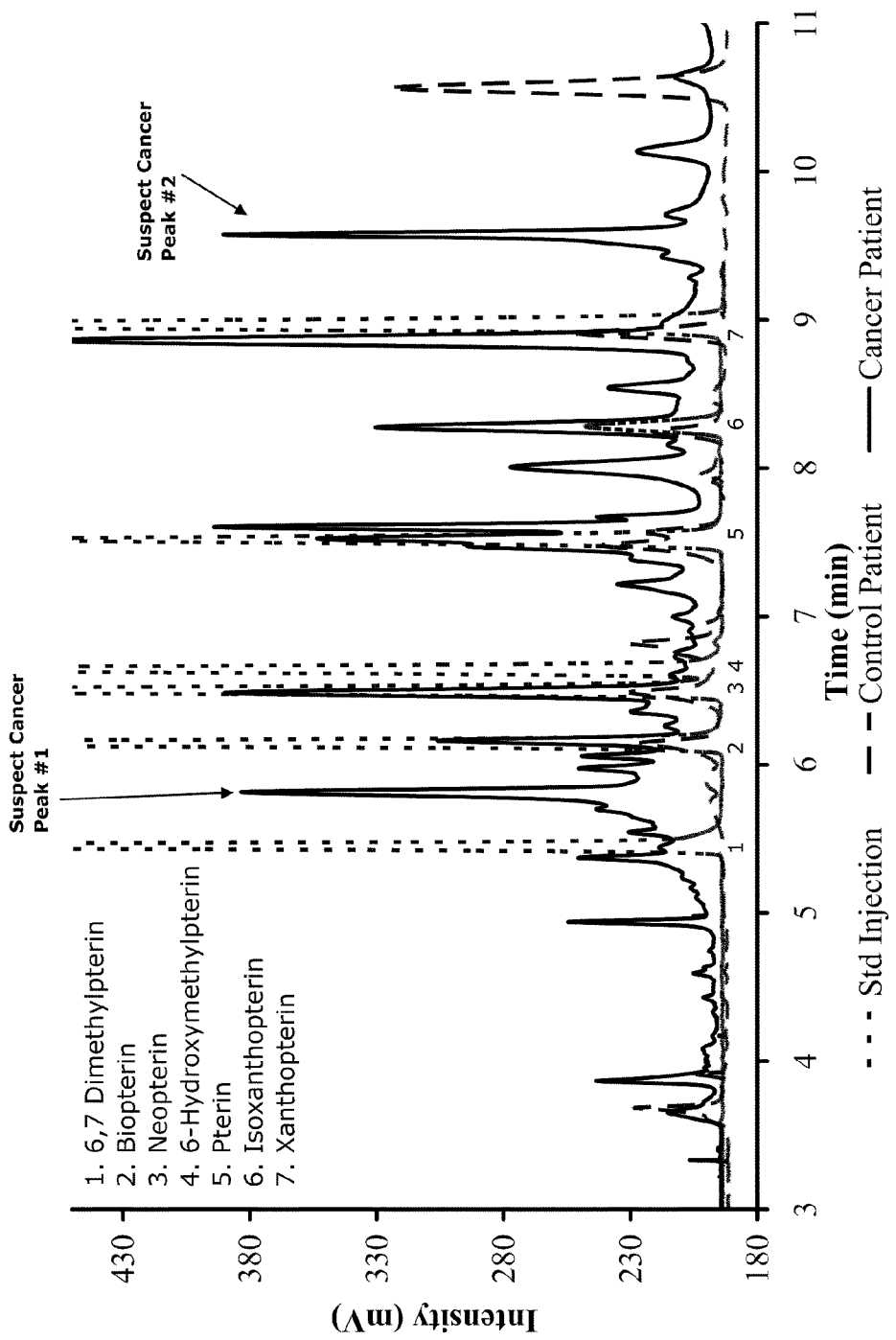
FIG. 14 is an electrophergram generated according to Example 2.

The foregoing method was also performed to analyze for cancer by detection of oncopterin. Cancer and cancer-free urine samples were analyzed and plotted as shown in FIG. 14. The experimental conditions were as follows: Running buffer: 0.1 M Tris-0.1 M borate-2 mM EDTA, pH 9.63; Capillary: 50 mm i.d.×70 cm (35 cm effective column length); Injection: gravimetric (17.5 cm from the of the sample to the instrument table and the injection time was 10 seconds). Running voltage: 371 V/cm; LIF detection at 325 nm/445 nm (ex/em); concentration of each pteridine standard: $1.0 \times 10^{-9}$ M. FIG. 14 shows these eight known peaks in the cancer samples and has them labeled 1-8: 1) 6,7-dimethylpterin; 2) 6-biopterin; 3) D-(+)-neopterin; 4) 6-hydroxymethylpterin; 5) Pterin; (6) isoxanthopterin; 7) xanthopterin; (8) carboxypterin. FIG. 14 also shows two peaks not identified with any of (1) through (8).

Previous work shows that oncopterin is elevated in patients with cancer. Since this experiment ran cancer and control samples side-by-side, one would expect to see a distinct different between the electropherograms. The peak between the peaks labeled 1 (6,7 DMP) and 2 (biopterin) is expected to identify oncopterin in view of the structural similarity between oncopterin and biopterin. It is expected this will be confirmed by analysis of an oncopterin standard. Consistent with this identification is that propylamine which differentiates oncopterin from biopterin could shift its elution time in an unpredictable manner, which would manifest itself in the second peak marked with an arrow in FIG. 14.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

What is claimed is:

1. A method for screening for cancer in a mammal, the method comprising:
    obtaining a biological sample from the mammal;
    treating the biological sample with an oxidizing agent in a concentration sufficient such that at least about 90 wt % of concentration of oncopterin (N2-(3-aminopropyl) biopterin) in the biological sample is in its fully oxidized state;
    quantitatively measuring a concentration of oncopterin (N2-(3-aminopropyl) biopterin) in said biological sample by capillary electrophoresis-lased induced fluorescence by subjecting the sample to capillary electrophoresis using laser-induced fluorescence (CE-LIF) to cause the oxidized portion of said concentration of said oncopterin (N2-(3-aminopropyl) biopterin) to emit fluorescent light, detecting the emitted fluorescence light, and analyzing the emitted fluorescence light to determine the concentration of the oncopterin (N2-(3-aminopropyl) biopterin) in the biological sample; and
    comparing the concentration of oncopterin (N2-(3-aminopropyl) biopterin) in the sample to an expected concentration of oncopterin (N2-(3-aminopropyl) biopterin) for either a healthy or cancer-bearing mammal of the same species;
    wherein the CE-LIF comprises directing laser light through a filter, a focal lens, and an iris of a first optical system and into an electrophoresis capillary containing the biological sample to irradiate and cause fluorescence from the biological sample; and receiving fluorescence emission from the biological sample through a second optical system comprising a confocal lens having a magnification greater than 20× and an iris which focus emitted fluorescence onto a photomultiplier tube as a light collection device for collecting fluorescent light emitted from the pteridine in the biological sample.

2. The method of claim 1 wherein the biological sample is a urine sample.

3. The method of claim 1 wherein the subjecting the sample to CE-LIF comprises:
    injecting the biological sample containing the oxidized portion of pteridine into a capillary;
    electrophoretically separating the oxidized portion of pteridine in the capillary by applying an electric field having a minimum voltage of 10 kV; and
    irradiating the separated sample with non-polarized laser light from an excitation source having a power output of at least 1 mW.

4. The method of claim 1 wherein the treating the biological sample with the oxidizing agent is in a concentration sufficient such that at least about 95 wt % of said concentration of said pteridine compound in the biological sample is in its fully oxidized state.

5. The method of claim 1 wherein the treating the biological sample with the oxidizing agent is in a concentration sufficient such that at least about 99 wt % of said concentration of said pteridine compound in the biological sample is in its fully oxidized state.

6. The method of claim 1 wherein the pteridine compound concentration is quantitatively oxidized by contacting the biological sample with elemental iodine.

7. The method of claim 1 wherein the biological sample is combined with a sample matrix having a high ionic strength.

8. The method of claim 7 wherein the sample matrix is phosphate buffer.

9. The method of claim 1 further comprising detecting concentration levels of pteridine compounds other than oncopterin to determine what type of cancer that the mammal may develop.

10. The method of claim 1 wherein the CE-LIF causes the oncopterin to be separated from other species in the biological sample matrix.

11. A method for screening for cancer in a mammal, the method comprising:
    obtaining a biological sample from the mammal;
    treating the biological sample with an oxidizing agent in a concentration sufficient to fully oxidize oncopterin (N2-(3-aminopropyl) biopterin) in the biological sample;
    quantitatively measuring a concentration of oncopterin (N2-(3-aminopropyl) biopterin) in said biological sample by capillary electrophoresis-lased induced fluorescence by subjecting the sample to capillary electrophoresis using laser-induced fluorescence (CE-LIF) to cause the oxidized portion of said concentration of said oncopterin (N2-(3-aminopropyl) biopterin) to emit fluorescent light, detecting the emitted fluorescence light, and analyzing the emitted fluorescence light to determine the concentration of the oncopterin (N2-(3-aminopropyl) biopterin) in the biological sample; and comparing the concentration of oncopterin (N2-(3-aminopropyl) biopterin) in the sample to an expected concentration of oncopterin (N2-(3-aminopropyl) biopterin) for either a healthy or cancer-bearing mammal of the same species;

wherein the CE-LIF comprises directing laser light through a filter, a focal lens, and an iris of a first optical system and into an electrophoresis capillary containing the biological sample to irradiate and cause fluorescence from the biological sample; and receiving fluorescence emission from the biological sample through a second optical system comprising a confocal lens having a magnification greater than 10× and an iris which focus emitted fluorescence onto a photomultiplier tube as a light collection device for collecting fluorescent light emitted from the pteridine in the biological sample.

* * * * *